(12) United States Patent
Impero et al.

(10) Patent No.: US 10,123,878 B2
(45) Date of Patent: Nov. 13, 2018

(54) ANKLE PROSTHESIS

(71) Applicants: Anna Impero, Sinnai (IT); CIQUADRO SNC DI CARBONI SEBASTIANO, Cagliari (IT); Hans-Peter Abt, Oberursel (DE); FH ORTHOPEDICS, Heimsbrunn (FR); FOURNITURES HOSPITALIERES INDUSTRIE, Quimper (FR)

(72) Inventors: Anna Impero, Sinnai (IT); Anna Cossu, Capoterra (IT); Hans-Peter Abt, Oberursel (DE)

(73) Assignees: Anna Impero, Sinnai (CA) (IT); CIQUADRO SNC DI CARBONI SEBASTIANO, Cagliari (IT); Hans-Peter Abt, Oberursel (DE); FH ORTHOPEDICS, Heimsbrunn (FR); FOURNITURES HOSPITALIERES INDUSTRIE, Quimper (FR)

( * ) Notice: Subject to any disclaimer, the term of this patent is extended or adjusted under 35 U.S.C. 154(b) by 0 days.

(21) Appl. No.: 15/025,495

(22) PCT Filed: Sep. 26, 2014

(86) PCT No.: PCT/EP2014/070662
§ 371 (c)(1),
(2) Date: Mar. 28, 2016

(87) PCT Pub. No.: WO2015/044373
PCT Pub. Date: Apr. 2, 2015

(65) Prior Publication Data
US 2017/0143500 A1    May 25, 2017

(30) Foreign Application Priority Data
Sep. 26, 2013 (IT) .............................. MI2013A1590

(51) Int. Cl.
*A61F 2/42* (2006.01)
*A61B 17/17* (2006.01)
*A61F 2/30* (2006.01)

(52) U.S. Cl.
CPC ........ *A61F 2/4202* (2013.01); *A61B 17/1775* (2016.11); *A61F 2002/30158* (2013.01);
(Continued)

(58) Field of Classification Search
CPC ............ A61F 2/4202; A61F 2002/4205; A61F 2002/4207; A61F 2002/30884
See application file for complete search history.

(56) References Cited

U.S. PATENT DOCUMENTS

| | | | |
|---|---|---|---|
| 4,323,080 A | 4/1982 | Melhart | |
| 4,827,496 A | 5/1989 | Cheney | |

(Continued)

FOREIGN PATENT DOCUMENTS

EP        1779790 A2    5/2007

OTHER PUBLICATIONS

International Search Report dated Feb. 12, 2015 re: Application No. PCT/EP2014/070662; pp. 1-6; citing: U.S. Pat. No. 5,324,106 A, US 2006/247788 A1, US 2008/215156 A1, US 2004/002768 A1, U.S. Pat. No. 8,491,596 B2, EP 1 779 790 A2, US 2012/130376 A1, US 2006/142870 A1, U.S. Pat. No. 4,827,496 A, U.S. 4,323,080 A.
(Continued)

*Primary Examiner* — Brian Dukert
(74) *Attorney, Agent, or Firm* — Cantor Colburn LLP

(57) ABSTRACT

Ankle prosthesis (400) comprising a tibial component (100), a talar component (200) and an intermediate component (300) interposed between said tibial component (100) and said talar component (300). The prosthesis has an anatomical shape and enables restoration of articular functionalities. Also described are a tool for the shaping of a talus, which (Continued)

shaping is aimed at the implant of the talar component (200) of said prosthesis (400), and a surgical tool for enabling a shaping of the tibia aimed at the implantation of the tibial component (100).

11 Claims, 13 Drawing Sheets

(52) U.S. Cl.
CPC ............... *A61F 2002/30398* (2013.01); *A61F 2002/30604* (2013.01); *A61F 2002/30884* (2013.01); *A61F 2002/30892* (2013.01); *A61F 2002/4205* (2013.01); *A61F 2002/4207* (2013.01)

(56) References Cited

U.S. PATENT DOCUMENTS

| | | | |
|---|---|---|---|
| 5,824,106 A * | 10/1998 | Fournol | A61F 2/4202 623/21.18 |
| 7,025,790 B2 * | 4/2006 | Parks | A61B 17/15 623/21.11 |
| 8,491,596 B2 | 7/2013 | Long et al. | |
| 2004/0002768 A1 | 1/2004 | Parks et al. | |
| 2006/0142870 A1 | 6/2006 | Robinson et al. | |
| 2006/0247788 A1 * | 11/2006 | Ross | A61F 2/4202 623/21.18 |
| 2008/0215156 A1 | 9/2008 | Duggal et al. | |
| 2012/0130376 A1 | 5/2012 | Loring et al. | |
| 2014/0128985 A1 * | 5/2014 | Sanders | A61F 2/4225 623/21.18 |
| 2015/0045902 A1 * | 2/2015 | Perler | A61F 2/4202 623/21.18 |

OTHER PUBLICATIONS

Written Opinion dated Feb. 12, 2015 re: Application No. PCT/EP2014/070662; pp. 1-12; citing: U.S. Pat. No. 5,824,106 A, US 2006/247788 A1, US 2008/215156 A1, US 2004/002768 A1, U.S. Pat. No. 8,491,596 B2, EP 1 779 790 A2, US 2012/130376 A1, US 2006/142870 A1, U.S. Pat. No. 4 827 496 A, U.S. Pat. No. 4,323,080 A.

* cited by examiner

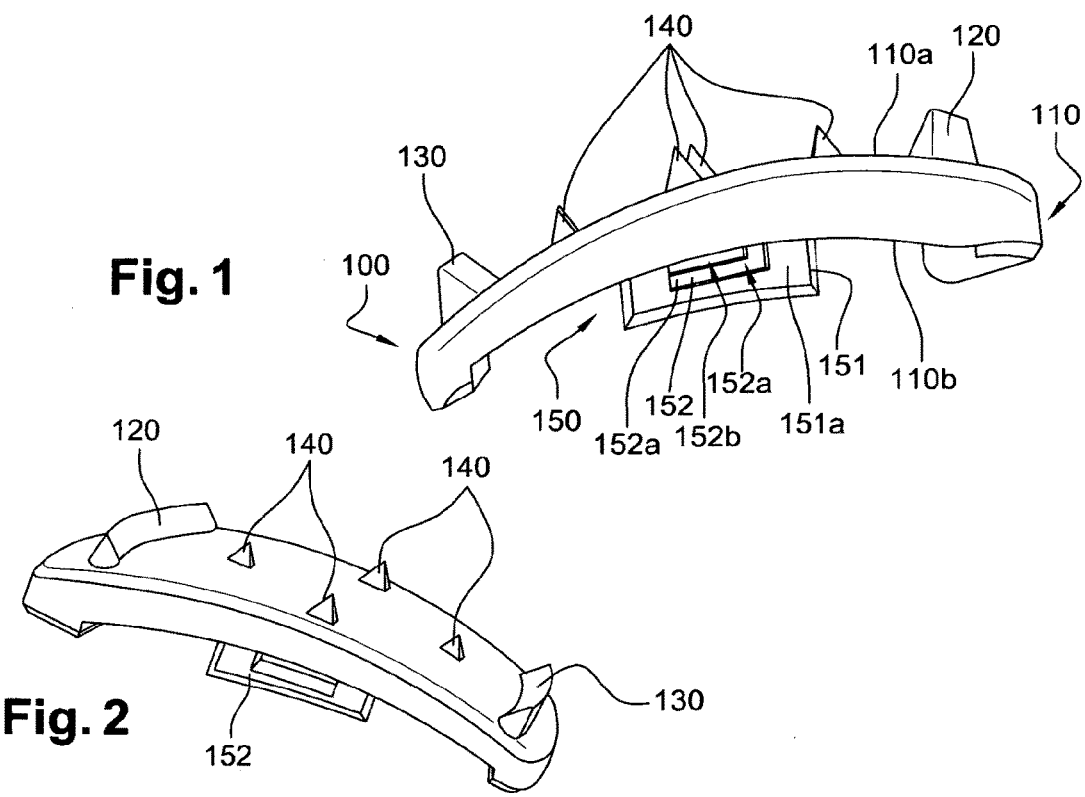
Fig. 1
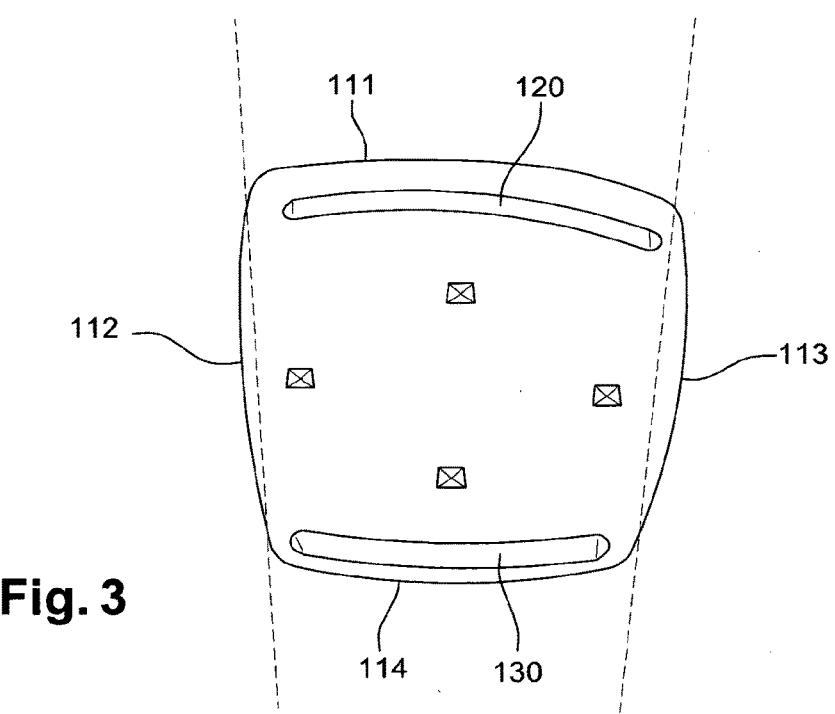
Fig. 2
Fig. 3

ANKLE PROSTHESIS

TECHNICAL FIELD

The present invention relates to an ankle prosthesis.

The present invention also relates to a tibial component for said prosthesis.

The present invention also relates to a talar component for said prosthesis.

The present invention moreover relates to a tool for the shaping of a talus aimed at the application of said prosthesis.

BACKGROUND ART

As is known there exist several circumstances, of traumatic and/or pathological nature, which involve the application of a prosthesis of the ankle.

This prosthesis is set between the terminal part of the tibia and the upper part of the talus, to replace the original articulation in all respects.

The ankle prostheses typically comprise a tibial component, which is fixed to the terminal part of the tibia, and a talar component, which is fixed to the upper part of the talus. Between the tibial component and the talar component a third component is interposed, suitably shaped so as to enable the first two components to move reciprocally and hence provide, from the mechanical viewpoint, functionalities similar to those typically provided by a natural articulation.

Applicants have noted that the prostheses available nowadays imply surgical operations of application which are considerably complicated, both in terms of access to the area at which the operation is required, and in terms of machining/shaping of the bones to which the components of the prosthesis have to be secured.

For example, some prostheses require a lateral-type operation, which involves removal of some intact and functional bone portions (e.g. fibula), which otherwise would not be affected by the surgical operation.

These prostheses also require forming a pair of grooves (imagining the patient in a standing position, these grooves are arranged horizontally and transversely to the direction in which the patient would walk) in the terminal part of the tibia. Also this machining operation, besides being complex from the viewpoint of its execution, causes a very in-depth machining of a portion of a substantially healthy bone.

From the viewpoint of the talar component, it often requires a multiplicity of steps of cutting/shaping of the talus, which renders the surgical operation further complex and risky.

In fact, the drawbacks mentioned above, besides impacting on the difficulty of the operation in general, also involve risks both for the patient (in case of a defective result of the intervention) and for the surgeon who performs the surgical intervention, from the viewpoint of his/her professional responsibility.

It should also be noted that, often, surgeons are not able to deal with an operation of this nature (which, moreover, requires a long learning curve), such that they fall back to the alternative consisting of the arthrodesis, i.e., the "joining" or "fusion" of the articulation. This leads to the permanent loss of the articular functionality and the ensuing condition of permanent disability. It is clear that this type of solution penalizes in an unacceptable way the patient, to whom a treatment of a completely different nature should be offered.

AIMS AND SUMMARY OF THE INVENTION

Therefore, the aim of the present invention is to provide an ankle prosthesis, and related components, which can be installed in a simpler manner, hence reducing the risks for the patient and for the surgeon.

In particular, the aim of the invention is to provide a prosthesis which can be installed using the so-called "frontal operation" technique, so as to avoid removal and subsequent reconstruction of bony portions not strictly related to the operation. In greater detail, the invention enables to implant an ankle prosthesis while maintaining intact the posterior malleolus of the tibia, also called Volkmann's Triangle or third malleolus.

Another aim of the invention is to enable installation of an ankle prosthesis by increasing—with respect to the state of the art—the stability and the optimal support of the system, while preserving the integrity of the trabecular structure of the bone.

A further aim of the invention is to provide a prosthesis that requires limited and simplified machining operations of the bony terminations to which the prosthesis has to be applied. In particular, a further aim of the invention is to enable the application of an ankle prosthesis by performing a limited number of cuts and/or millings on the bony end portions at which the prosthesis is to be positioned.

BRIEF DESCRIPTION OF THE DRAWINGS

These and still other aims are substantially achieved by an ankle prosthesis as described in the appended claims.

Further characteristics and advantages will become more apparent from the detailed description of a preferred and not exclusive embodiment of the invention.

Figure 4:
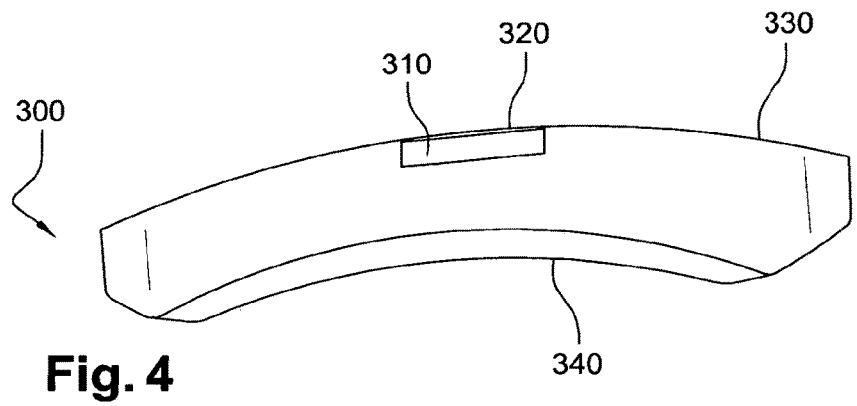
Figure 5:
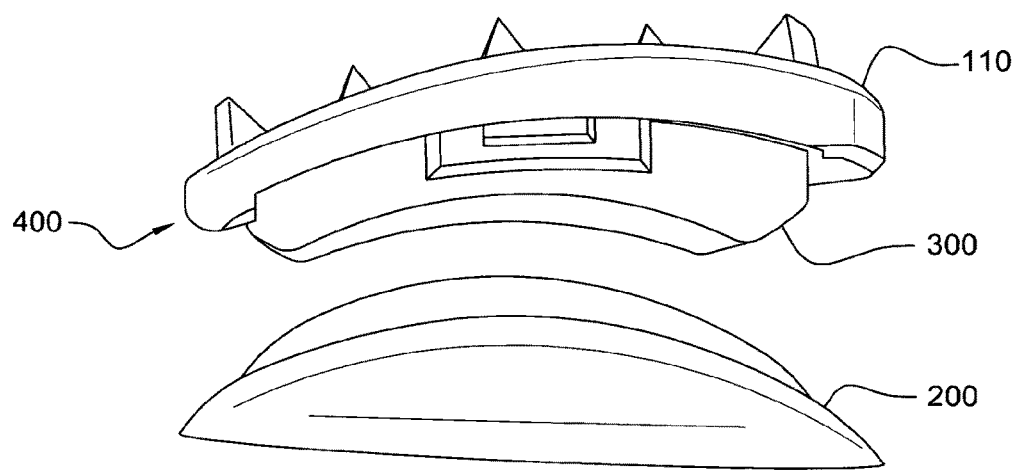
Figure 6:
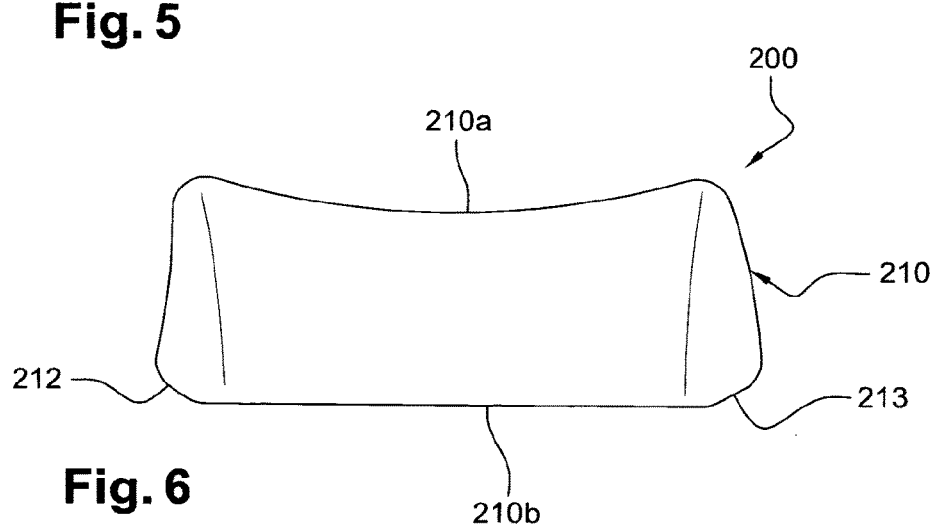
Figure 7:
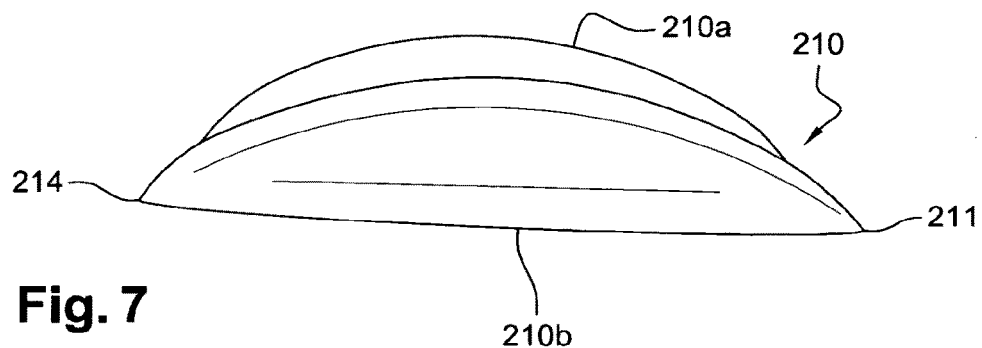
Figure 8:
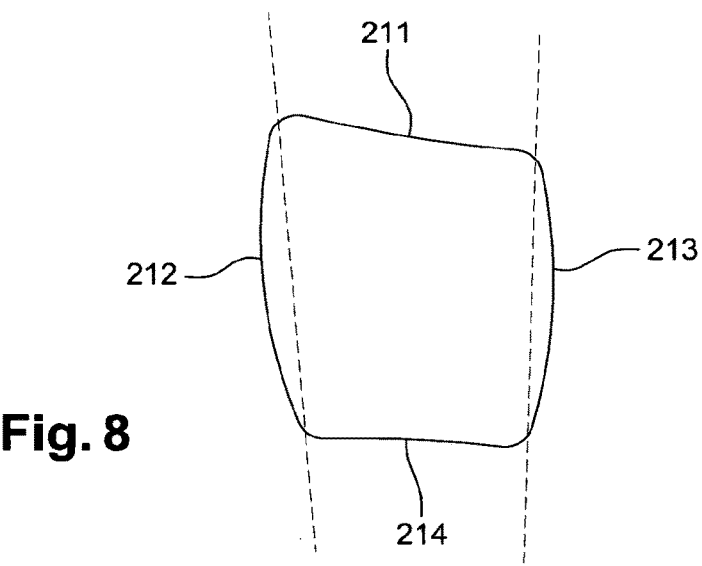
Figure 9:
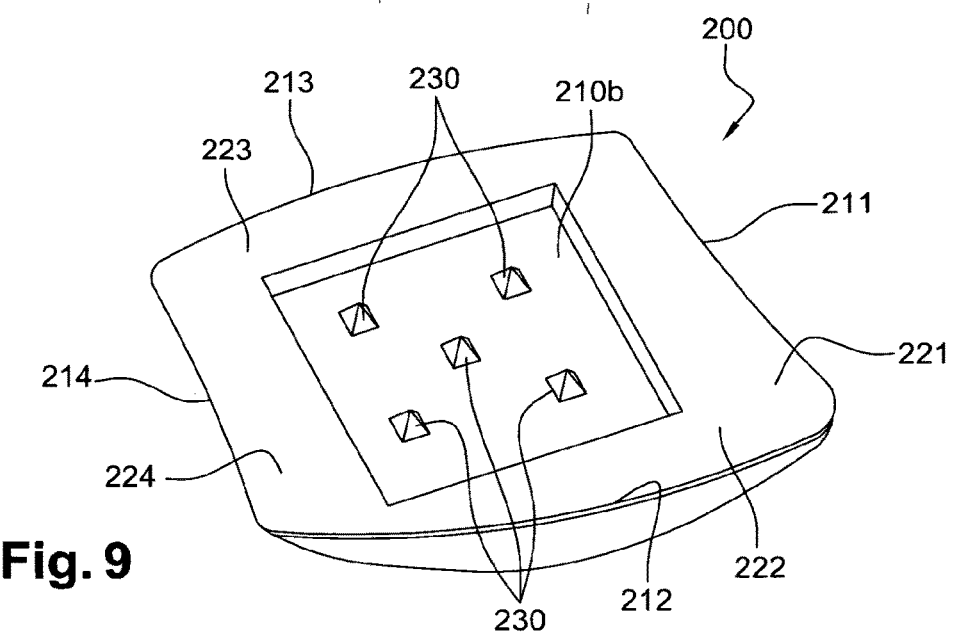
Figure 10:
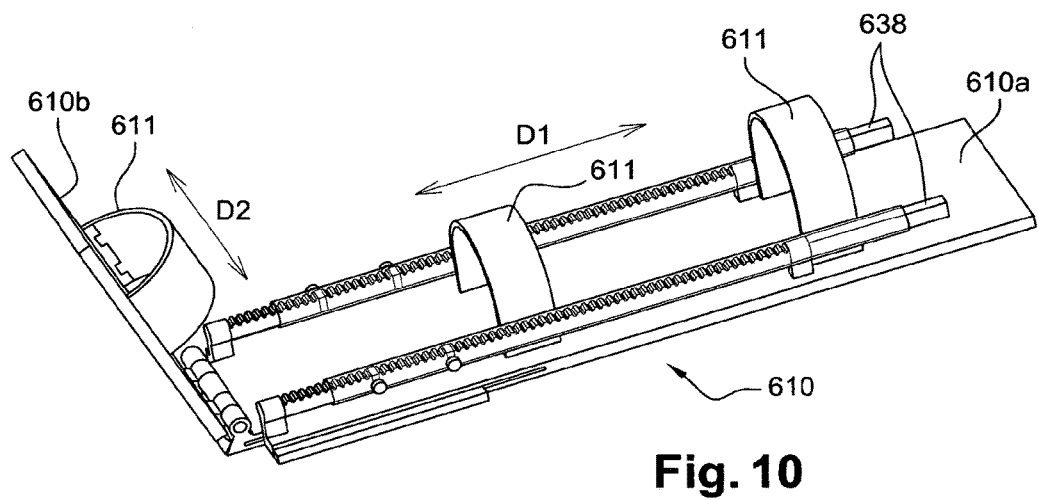
Figure 11:
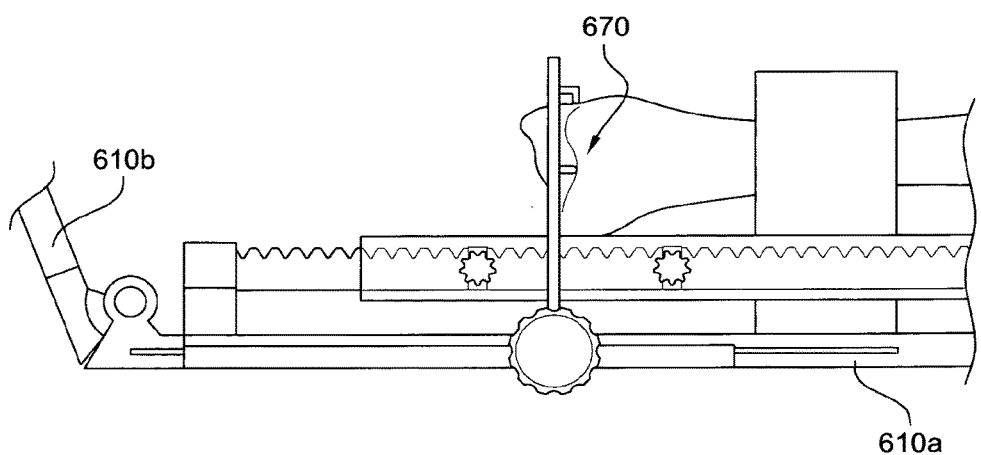
Figure 11A:
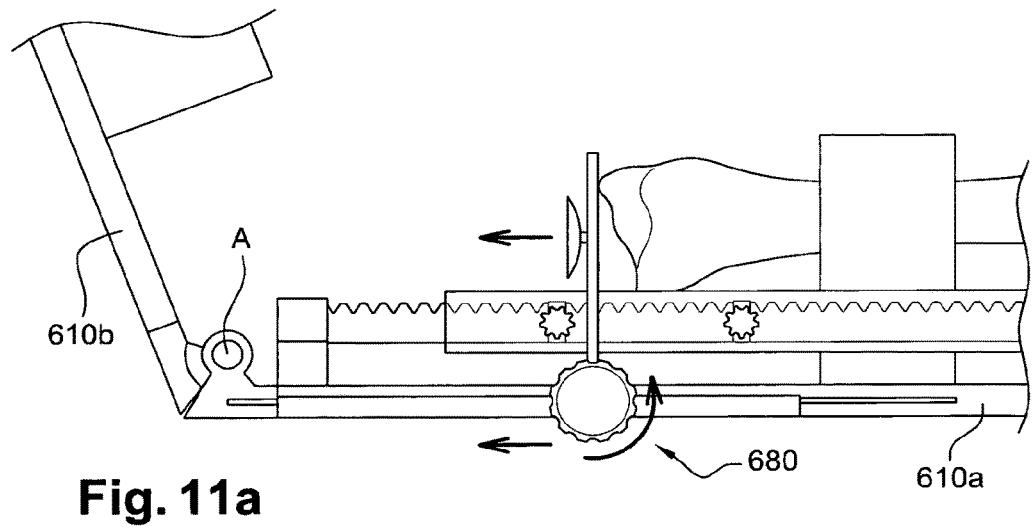
Figure 11B:
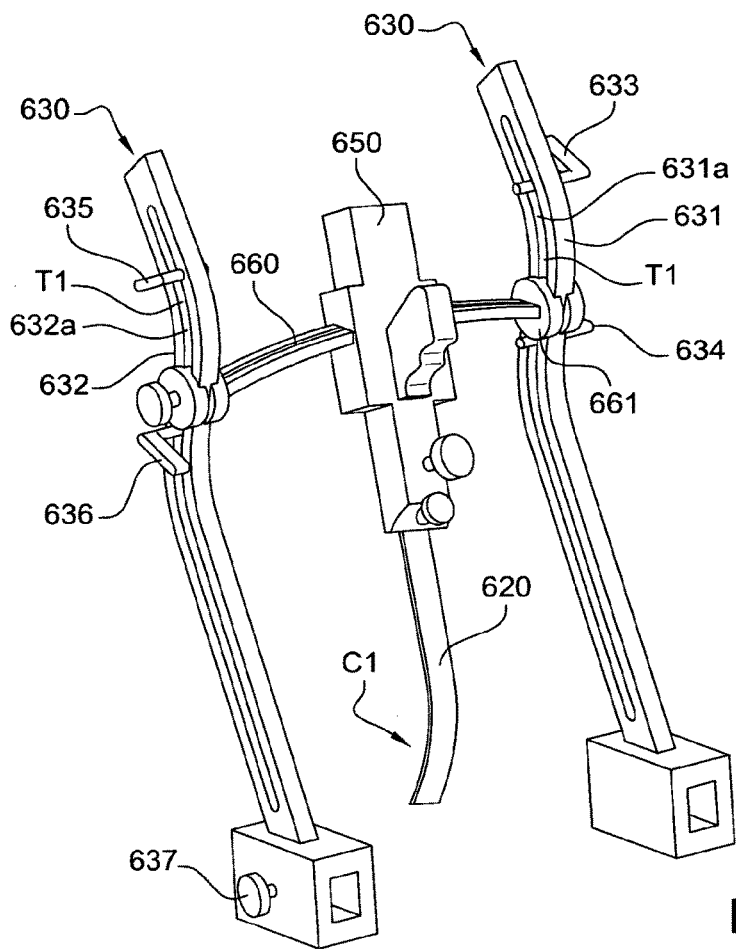
Figure 11C:
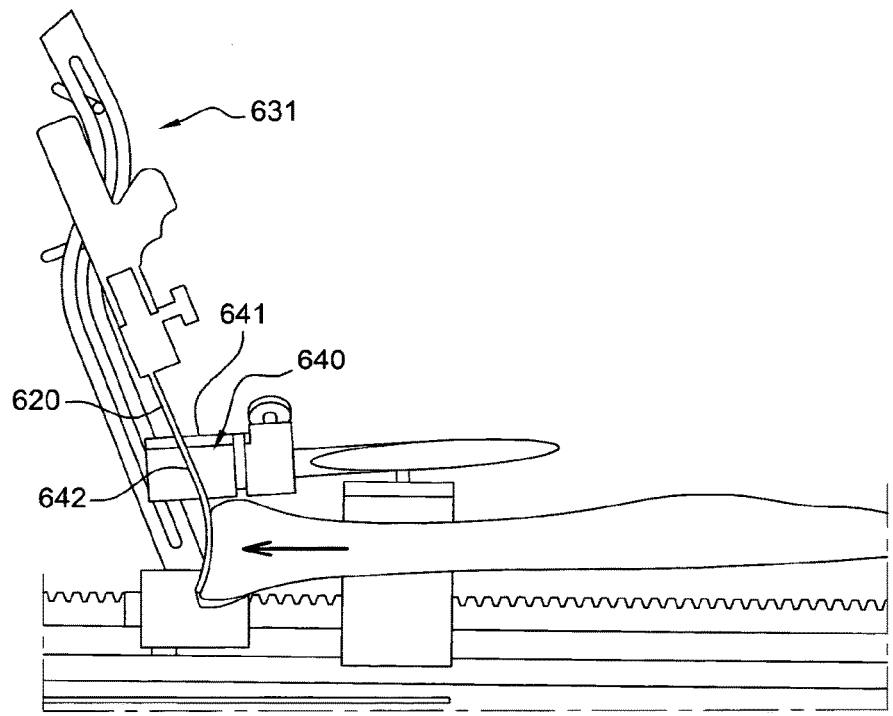
Figure 11D:
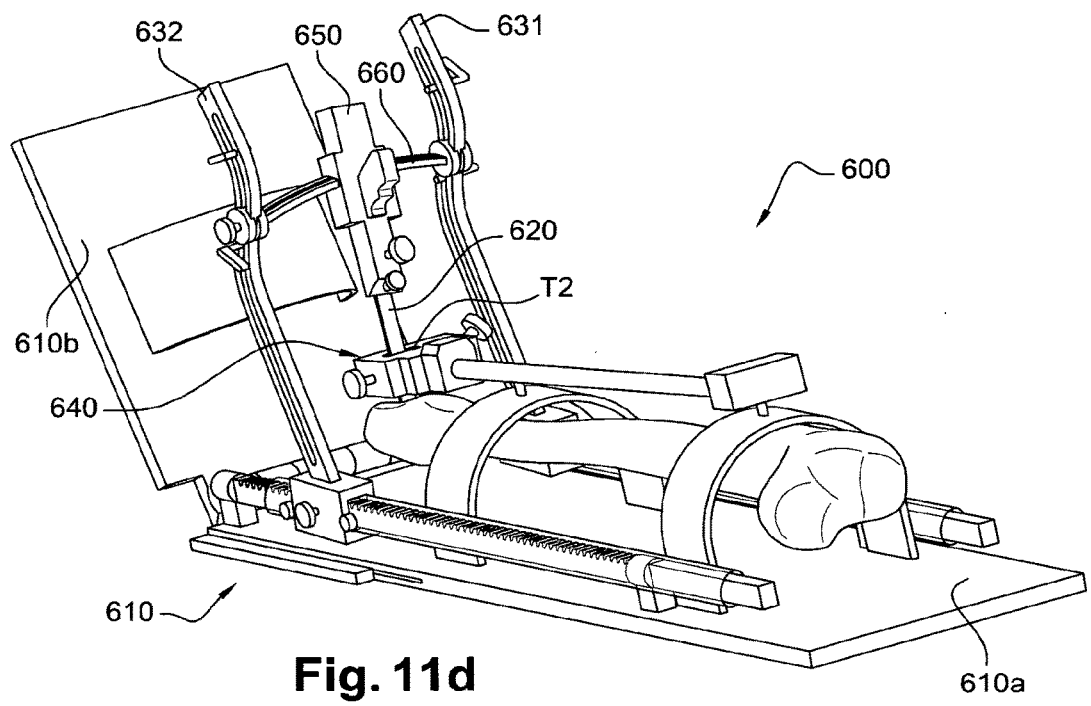
Figure 12:
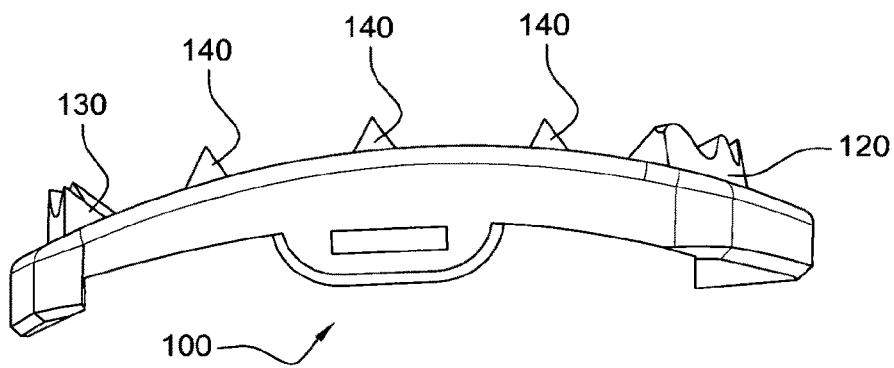
Figure 13:
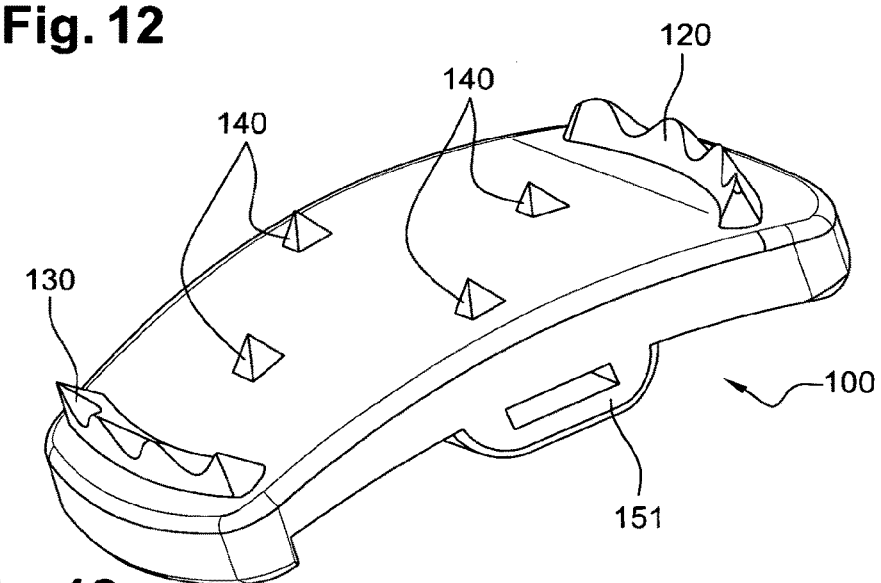
Figure 14:
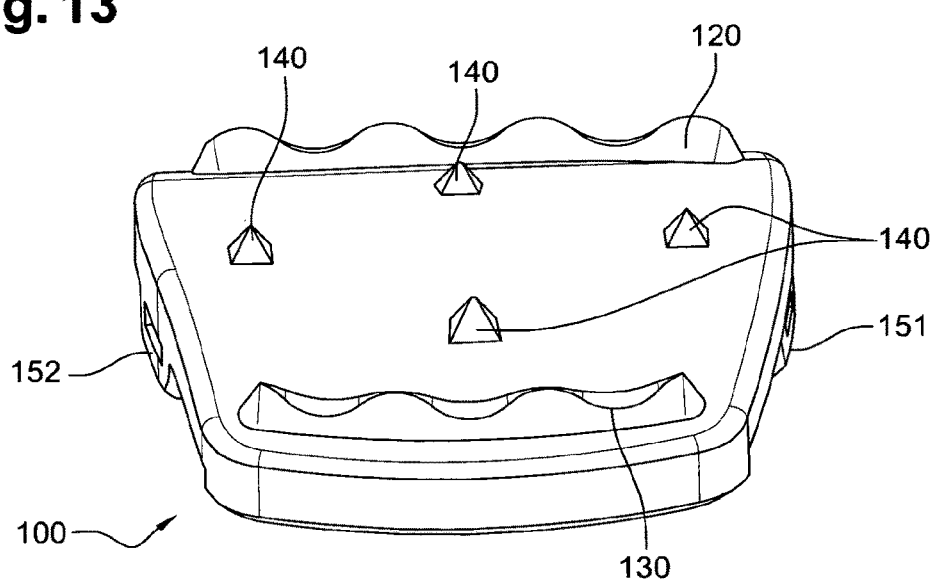
Figure 15:
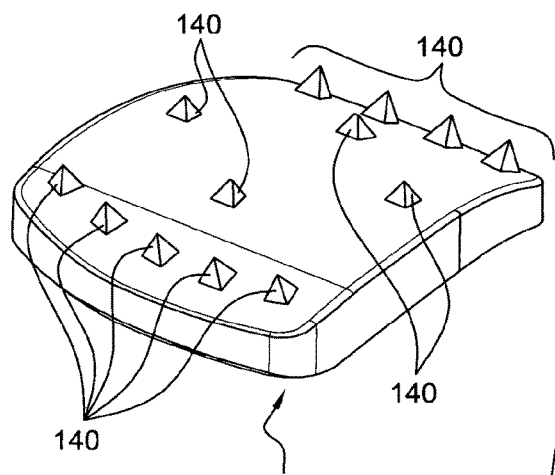
Figure 16:
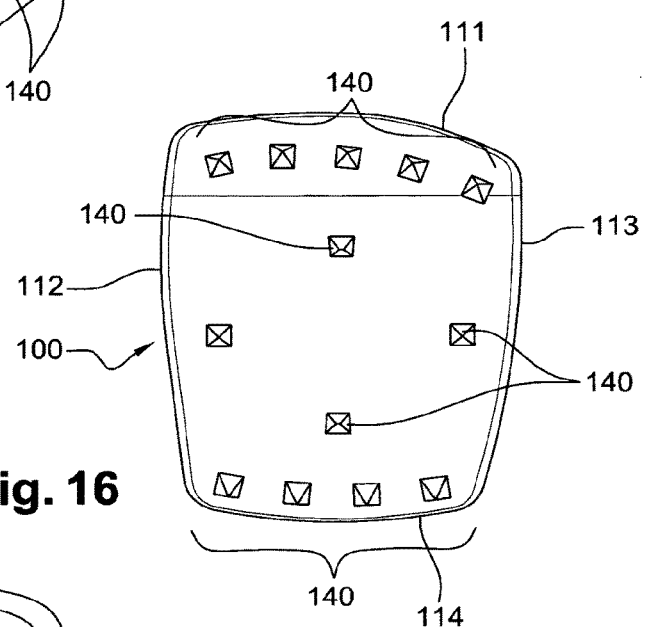
Figure 17:
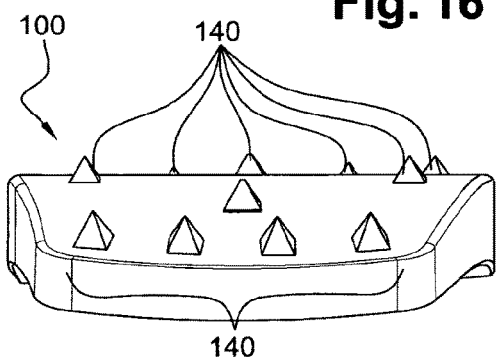
Figure 18:
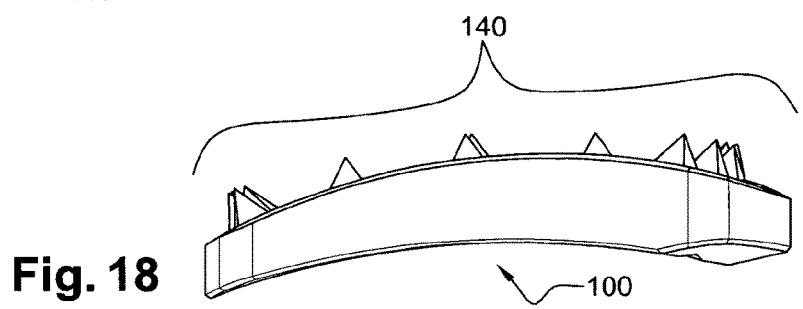
Figure 19:
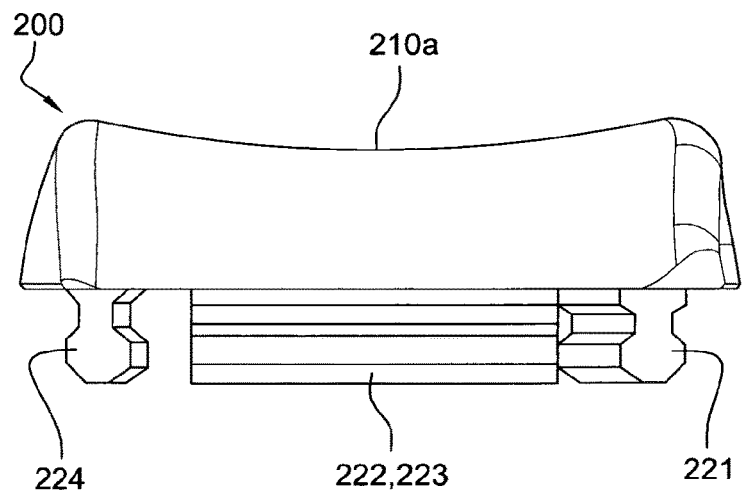
Figure 20:
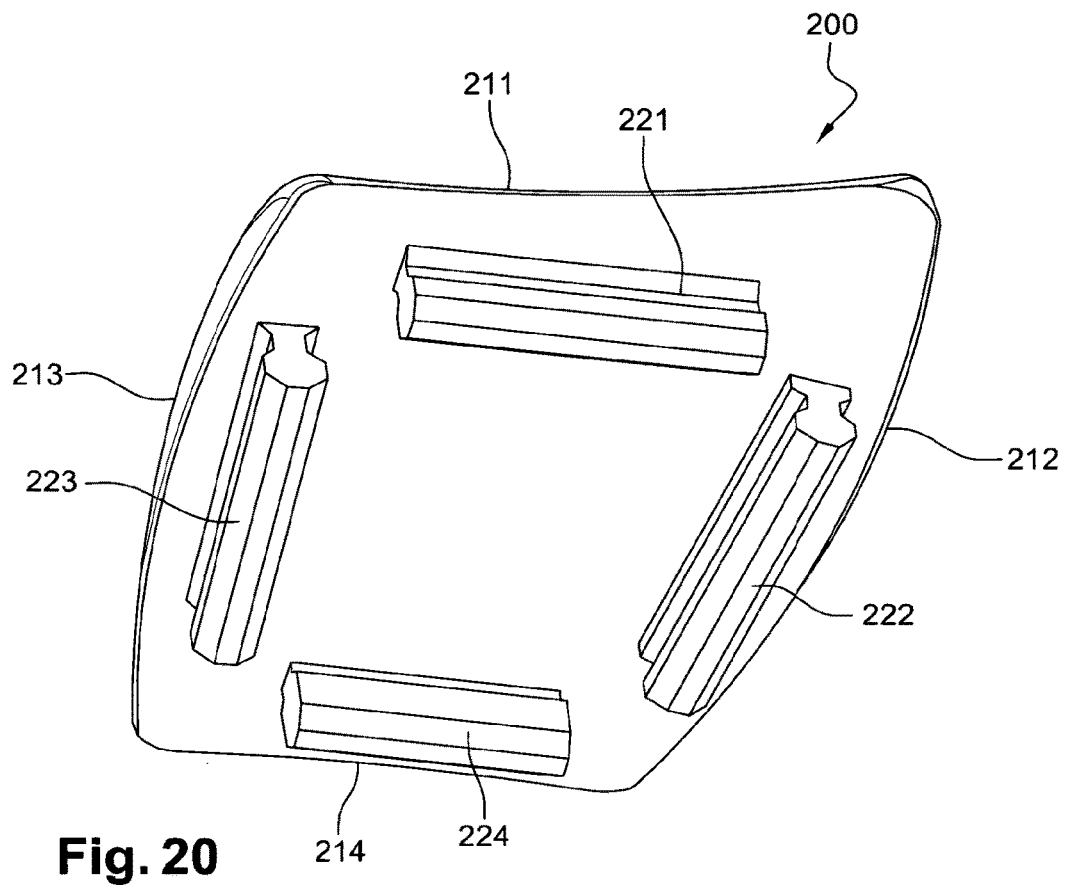
Figure 21:
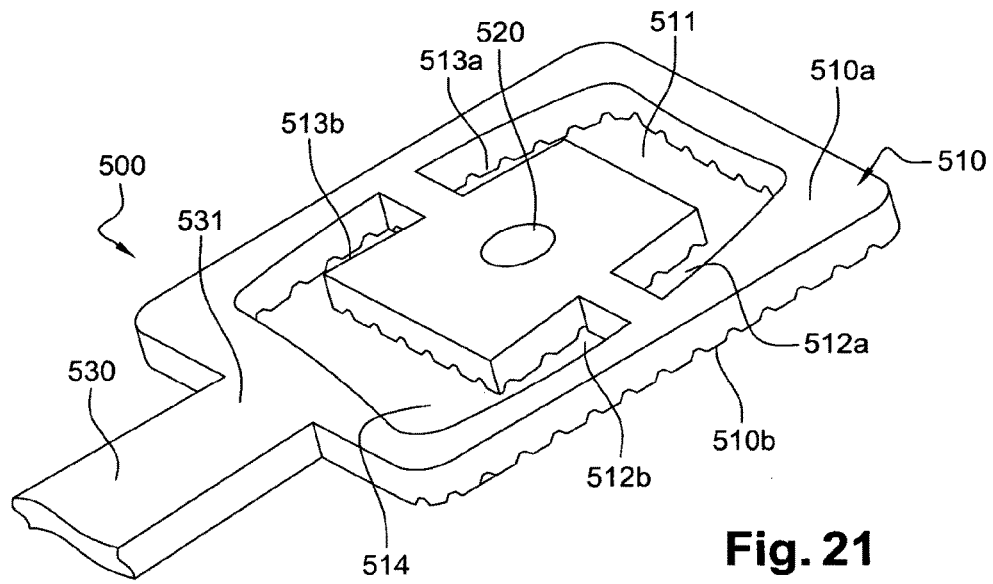
Figure 22:
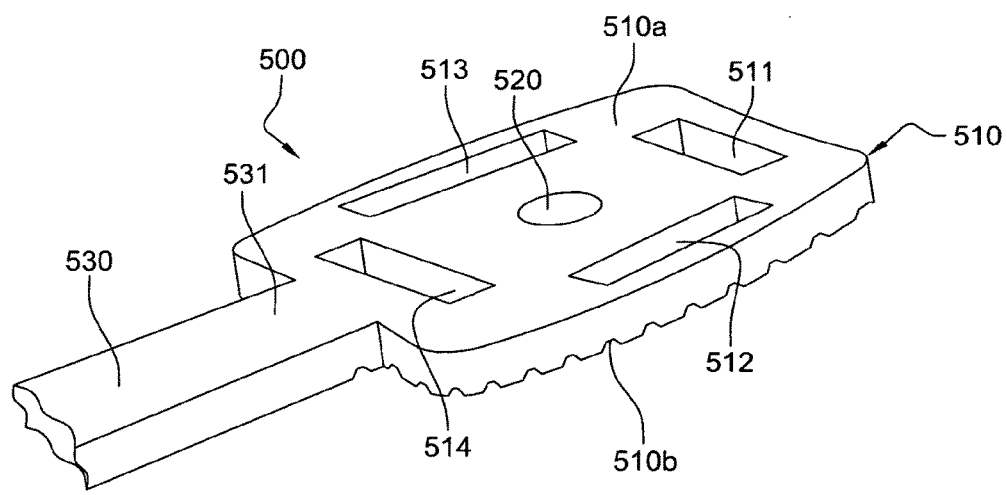

This description is provided herein below with reference to the accompanying figures, also having an exemplifying and non-limiting nature, in which:

FIG. 1 shows a side view of a tibial component of an ankle prosthesis in accordance with the present invention;

FIG. 2 shows the component of FIG. 1 in a perspective view;

FIG. 3 shows the component of FIGS. 1 and 2 in a plan view;

FIG. 4 shows a side view of an intermediate component of an ankle prosthesis in accordance with the present invention;

FIG. 5 shows an exploded view of an ankle prosthesis according to the present invention, comprising the tibial component of FIGS. 1-3 and the intermediate component of FIG. 4;

FIG. 6 shows a front view of a talar component of the ankle prosthesis according to the present invention;

FIG. 7 shows a side view of the talar component of FIG. 6;

FIG. 8 shows a top view of the talar component of FIGS. 6-7;

FIG. 9 shows a perspective view of the talar component of FIGS. 6-8;

FIG. 10 shows a frame forming part of a surgical apparatus according to the present invention;

FIGS. 11, 11a-11c show schematically parts or details of the surgical apparatus according to the present invention;

FIG. 11d shows a schematic perspective view of the surgical apparatus according to the present invention;

FIG. 12 shows a side view of another embodiment of a tibial component for the ankle prosthesis in accordance with the present invention;

FIG. 13 shows a perspective view of the tibial component of FIG. 12;

FIG. 14 shows a front view of the tibial component of FIGS. 12 and 13;

FIG. 15 shows a perspective view of a further embodiment of a tibial component for the ankle prosthesis in accordance with the present invention;

FIG. 16 shows a top view of the tibial component of FIG. 15;

FIG. 17 shows a front view of the tibial component of FIGS. 15-16;

FIG. 18 shows a side view of the tibial component of FIGS. 15-17;

FIG. 19 shows a side view of another embodiment of a talar component for the ankle prosthesis according to the present invention;

FIG. 20 shows a perspective view of the talar component of FIG. 19;

FIGS. 21-22 show two embodiments of a tool for the shaping of a talus, finalized to the implant of the talar component according to the present invention.

Figure 23:
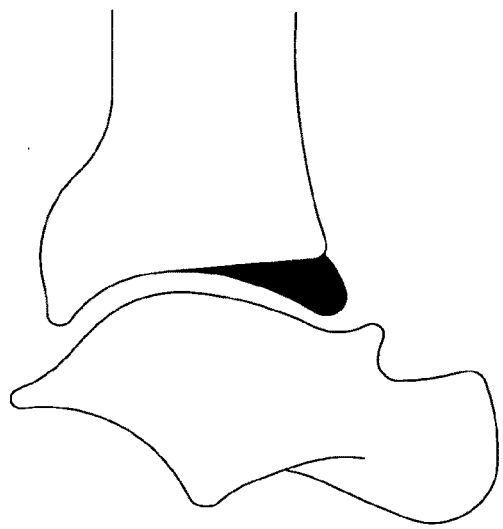

FIG. 23 shows a terminal portion of a patient's tibia before cutting.

Figure 24:
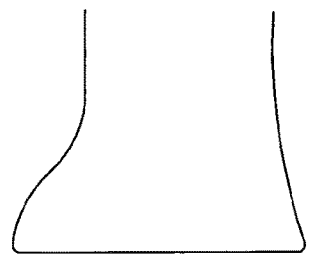

FIG. 24 shows a flat cutting of a tibial terminal portion performed with a surgical apparatus according to prior art.

Figure 25:
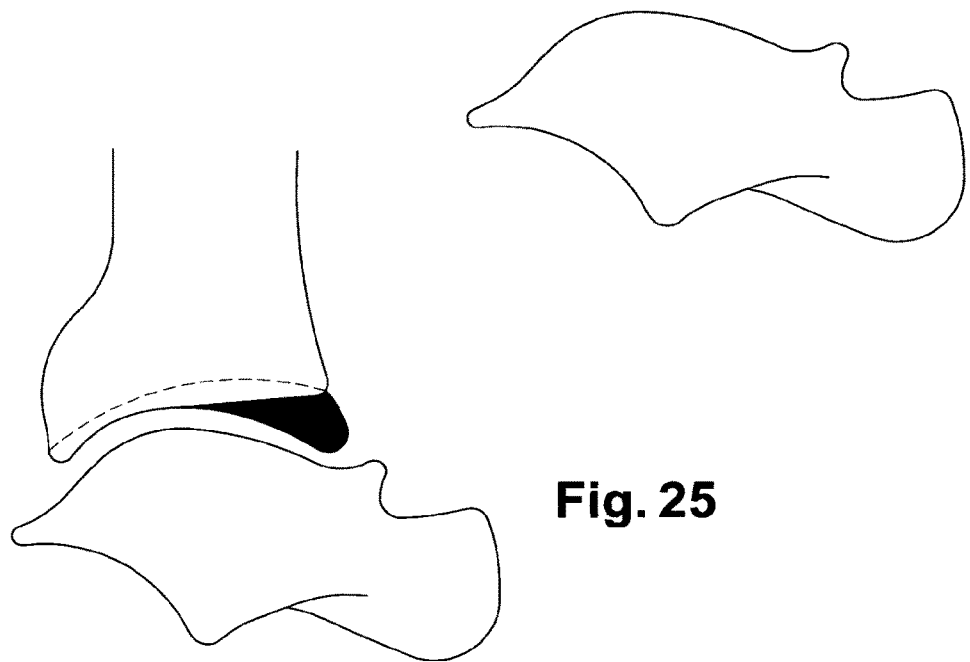

FIG. 25 shows a arched shape cutting of a tibial terminal portion performed with a surgical apparatus according to the present invention.

Figure 26:
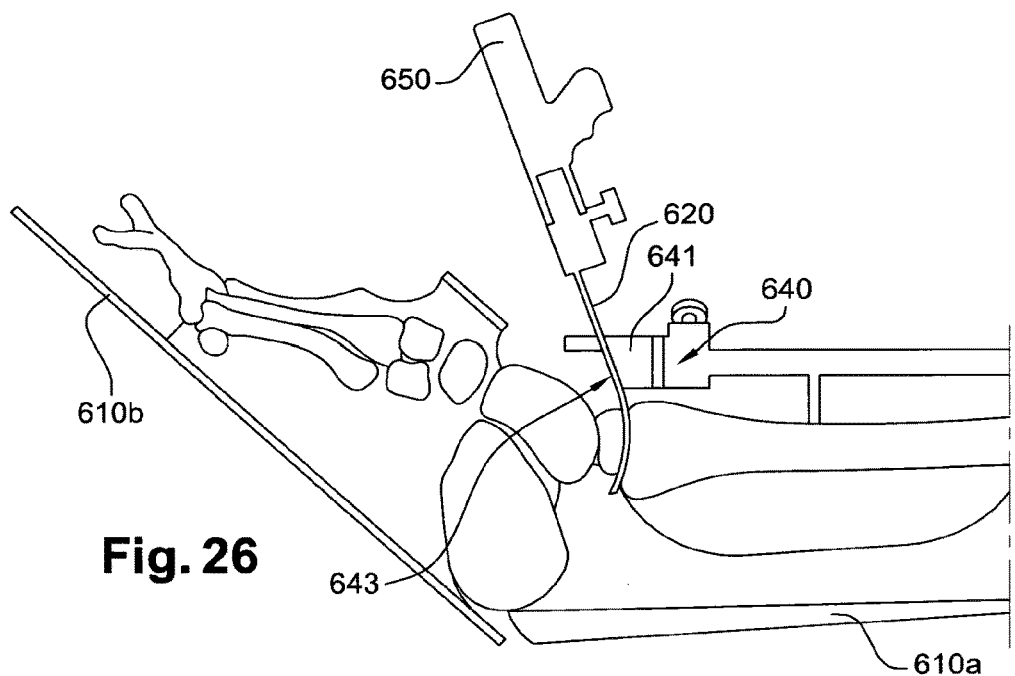
Figure 27:
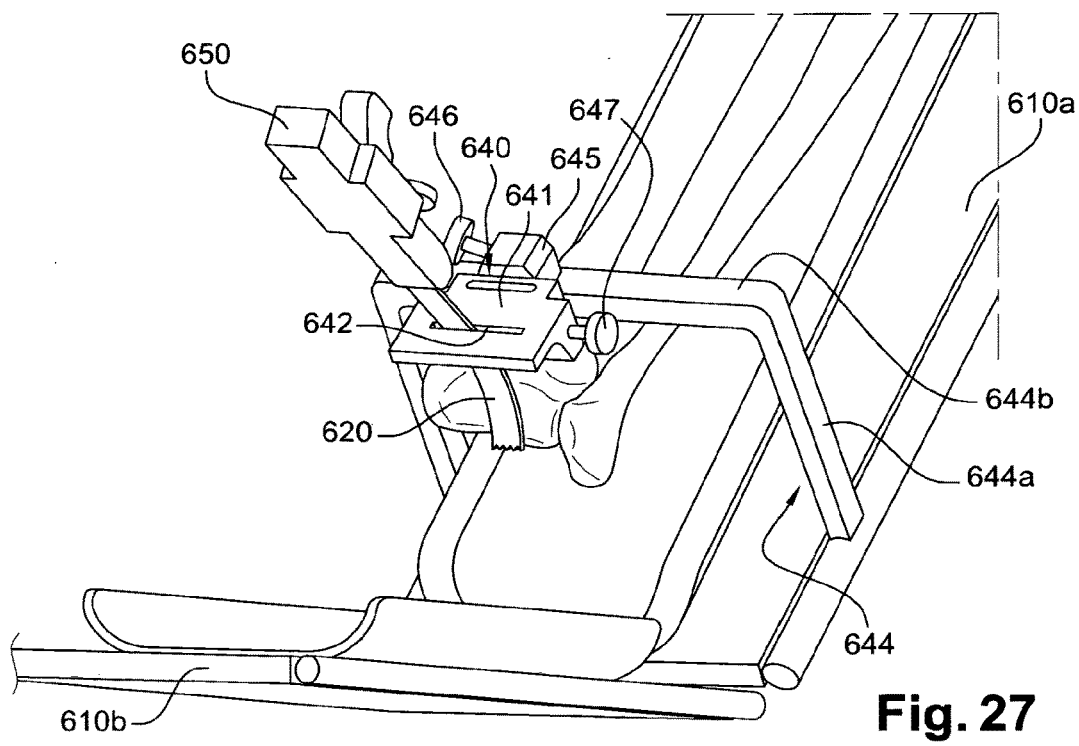
Figure 28:
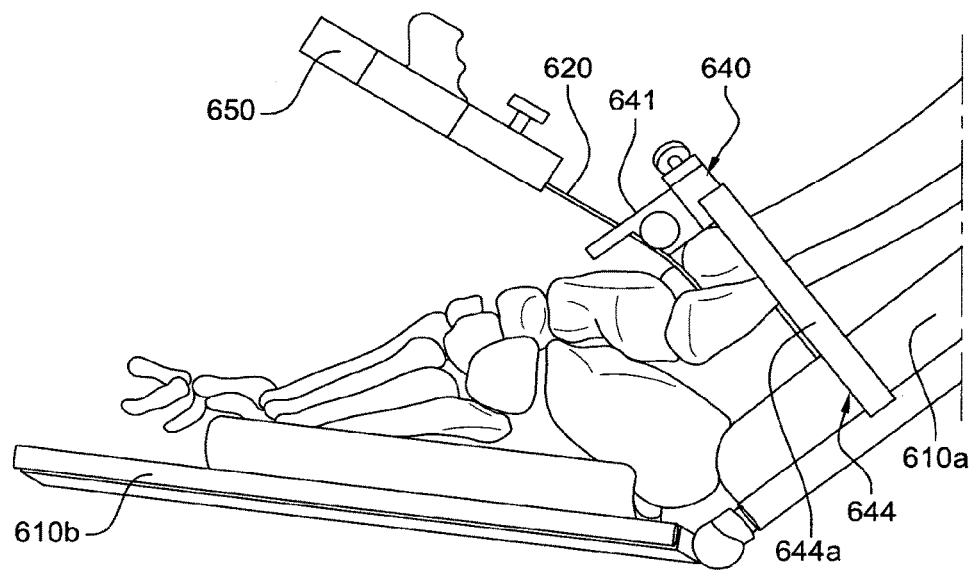
Figure 29:
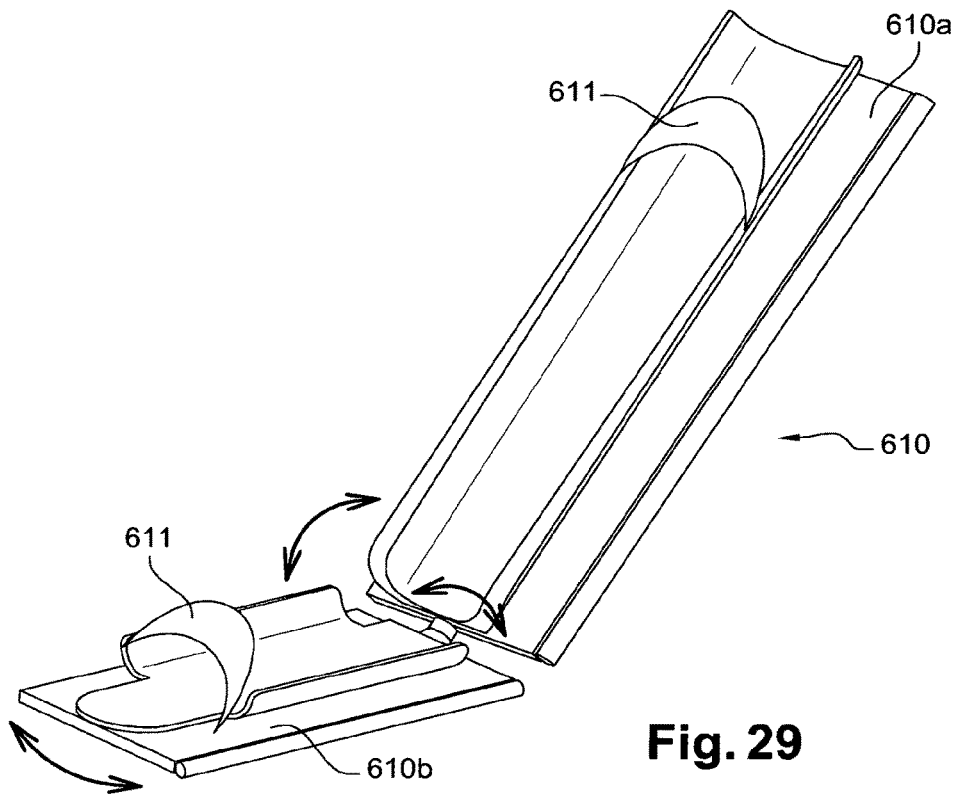

FIG. 26 shows details of a second embodiment of a surgical apparatus according to the present invention;

FIGS. 27 and 28 show details of a third embodiment of a surgical apparatus according to the present invention;

FIG. 29 shows a frame forming part of a fourth embodiment of the surgical apparatus.

DETAILED DESCRIPTION OF THE INVENTION

With reference to the accompanying figures, with 400 has been generally designated an ankle prosthesis according to the present invention.

The ankle prosthesis 400 (FIG. 5) comprises a tibial component 100 and a talar component 200, adapted to mutually cooperate in such a way that, after installation in a patient, they can allow movements substantially identical to those obtainable by the original bony articulation.

Preferably, as it will be more readily apparent in the following, the ankle prosthesis 400 also comprises an intermediate component 300, adapted to enable mutual cooperation and movement between the tibial component 100 and the talar component 200.

The tibial component 100 is configured to be fixed to the end of the tibia of the patient, in a position substantially facing the talus. The tibial component 100 can be a single-piece element.

The tibial component 100 can be made, for example, of chromium/cobalt, possibly with a coating made of titanium/plasma/spray or a similar coating.

In greater detail, the tibial component 100 (FIGS. 1-3) comprises a main body 110 having a substantially plate-shape.

The main body 110 has a top surface 110a and a bottom surface 100b.

The top surface 110a is adapted to engage with the end of the tibia.

The bottom surface 110b is adapted to engage with other components of the prosthesis 400, such as for example the aforementioned intermediate component 300 (FIGS. 4-5).

As schematically shown in FIG. 3, the main body 110 has, in a top view, a substantially quadrilateral profile, delimited by a front side 111, a pair of flanks 112, 113 and a rear side 114.

The front side 111 and/or the flank 112 and/or the flank 113 and/or the rear side 111 may be substantially curvilinear.

Preferably the front side 111, the flanks 112, 113 and the rear side 114 are substantially curvilinear so as to give the tibial component 100 an anatomical conformation.

Preferably, the front side 111 has a greater length than the rear side 114.

Preferably the development of the flanks 112, 113 is divergent from the rear side 114 to the front side 111. This divergent development is represented in FIG. 3 by a pair of dashed lines.

The top surface 110a, developing from the front side 111 to the rear side 114 has a curved profile, with its concavity facing towards the bottom surface 110b.

The bottom surface 110b has a development similar to that of the upper surface 110a, being substantially and approximately parallel to it.

Advantageously, the main body 110 has one or more expansions 120, 130, 140 that extend from the top surface 110a.

It should be noted that none of the expansions 120, 130, 140 comes in contact with the perimeter delimiting the top surface 110a. This perimeter is schematically represented by the combination of the front side 111 with the flanks 112, 113 and with the rear side 114.

In particular the expansions 120, 130, 140 are configured so as to enable an anchoring to the terminal part of the tibia, and to prevent transverse movements (i.e., along directions substantially orthogonal to the prevailing development of the tibia itself) of the tibial component 100 with respect to the tibia.

The expansions 120, 130 140 are adapted to be inserted in the inner part of the bony cortex of the tibia, thus ensuring stability with respect to the anterior/posterior displacement.

The expansions preferably comprise one or more fins, and in particular a front fin 120 and a rear fin 130, which extend according to profiles substantially transverse to the flanks 112, 113.

The front fin 120 is positioned in the front part of the main body 100, at the front side 111.

The rear fin 130 is positioned in the rear part of the main body 100, at the rear side 114.

Preferably the above mentioned expansions comprise one or more spikes 140, as schematically shown in FIGS. 1-3, having for example the shape of small pyramids.

FIGS. 12-14 and 15-18 illustrate two slightly different embodiments, in which (FIG. 12-14) the fins have a different shape, and in which (FIG. 15-18) the fins are substantially replaced by respective sequences of spikes.

In order to engage with the aforementioned intermediate component 300, the main body 110 can be provided with a suitable connection structure 150. Preferably said connection structure 150 enables a removable engagement between the tibial component 100 and the intermediate component 300. In this way it is possible to use an intermediate component 300 of appropriate dimensions, preferably adapted to the talar component 200.

In one embodiment the connection structure 150 comprises a pair of constraining elements 151, 152, each positioned at a respective flank 112, 113.

In particular, each constraining element 151, 152 may comprise a respective plate 151a, 152a with a respective slot 151b, 152b suitable for housing a corresponding expansion 310, 320 of the intermediate component 300.

It should be noted, for example, that the intermediate component 300 may be made of polyethylene.

Advantageously the top surface 330 of the intermediate component 300 is shaped substantially complementary to the bottom surface 110b of the main body 100 of the tibial component 100.

The talar component 200 (FIGS. 6-9 and 19-20) is configured to be fixed to the talus of the patient, in a position substantially facing the aforementioned end of the tibia. The talar component 200 can be a single-piece element.

The talar component 200 comprises a main body 210 having a top surface 210a and a bottom surface 210b.

The bottom surface 210b is substantially flat and substantially quadrilateral.

The bottom surface 210b is delimited by a front side 211, a first and a second flanks 212, 213 and a rear side 214.

At each side 211, 214 and at each flank 212, 213 there extends, from the bottom surface 210b, a respective expansion 221, 222, 223, 224 adapted to engage directly with a talus of a patient.

In one embodiment, the expansions 221, 222, 223, 224 are connected to one another in a substantial continuous fashion, as shown in FIG. 9.

In a different embodiment, the expansions 221, 222, 223, 224 are separated from each other, as shown in FIGS. 19-20.

In addition to the cited expansions, the main body 210 can further comprise one or more spikes 230 which extend from the bottom surface 210b in a region more central with respect to the expansions 221, 222, 223, 224.

Said one or more spikes may have, for example, the shape of small pyramids.

As schematically shown in FIG. 7, the top surface 210a has a curved shape developing from the front side 211 to the rear side 214, with its concavity facing towards the bottom surface 210b.

The top surface 210a is also curved, developing from the first flank 212 to second flank 213, with its convexity facing towards the bottom surface 210b.

In summary, the talar component 200 can present a substantially "saddle" shape, as regards its top surface 210a, so as to be perfectly anatomical and replace in an optimal manner the original upper portion of the talus.

As schematically shown in FIG. 8, the first flank 212 has a curvature larger than the second flank 213.

Preferably the front side 211 has a length greater than the rear side 214.

Advantageously, the upper surface 210a of the main body 210 of the talar component 200 is shaped substantially complementary to the bottom surface 340 of the intermediate component 300.

The talar component 200 can be made, for example, of chromium/cobalt, possibly with a coating in titanium/plasma/spray or similar coating.

In order to appropriately shape the top part of the talus, so as to enable a proper application of the above described talar component 200, a suitable tool 500 can be advantageously used.

Such a tool 500 for shaping a talus comprises an active portion 510, preferably mounted at one end 531 of a handle 530, the latter having a substantially elongated shape to enable easy use of the tool 500 itself.

The active portion 510 is substantially plate-shaped and has a top surface 510a and a bottom surface 510b, which are substantially parallel to each other and substantially parallel to the planar development of the active portion 510.

Preferably, the bottom surface 510b is corrugated to promote an engagement of the active portion 510 to the talus that is to be shaped.

The active portion 510 has a front recess 511, a rear recess 514, as well as first and second side recesses 512, 513. These recesses 511, 512, 513, 514 preferably have an elongated shape; should the active portion 510 have a substantially quadrilateral shape, then each recess 511, 512, 513, 514 would be advantageously substantially parallel to a respective side of said substantially quadrilateral shape.

Conveniently the recesses 511, 512, 513, 514 define a substantially quadrilateral profile.

In one embodiment, schematically shown in FIG. 21, the first side recess 512 comprises a front portion 512a and a rear portion 512a separated from each other; similarly, the second side recess 513 comprises a front portion 513a and a rear portion 513b separated from each other.

The front portion 512a of the first side recess 512 and the front portion 513a of the second side recess 513 are connected in a continuous fashion to the front recess 511, so as to form a first slot which is substantially "U"-shaped.

The rear portion 512a of the first side recess 512 and the rear portion 513b of the second side recess 513 are connected in a continuous fashion to the rear recess 514, so as to form a second slot which is substantially "U"-shaped and opposite to said first slot.

This embodiment can be advantageously used for shaping a talus before applying the talar component shown in FIG. 9.

In a different embodiment (FIG. 22), the front recess 511, the first and the second side recess and the rear recess 514 are separated from each other. In particular the recesses 511, 512, 513, 514 can be separated from each other by respective angular portions of the active portion 510.

This embodiment can be advantageously used for shaping a talus before applying the talar component shown in FIGS. 19-20.

Preferably, the active portion 510 may have a cavity 520 which is located inside the region delimited by the substantially quadrilateral profile formed by the four recesses 511, 512, 513, 514.

This cavity 520 can have, for example, a hemispherical shape.

The cavity 520 is advantageously adapted to engage with a distractor.

In order to apply the ankle prosthesis 400 to a patient, a suitable apparatus 600 can be used. The surgical apparatus 600 is preferably configured for ensuring a cutting of a tibia of a patient by a frontal approach.

The surgical apparatus 600 comprises firstly a frame 610 having a first portion 610a and a second portion 610b (FIG. 10. 11a, 11d).

The first portion 610a is adapted for the support of a leg of a patient, in particular in such a way that the leg remains stretched in a substantially horizontal direction.

The second portion 610b is adapted for the support of the patient's foot, in particular in a transverse direction with respect to the floor.

In practice, the first and the second portions 610a, 610b may be implemented as respective plate-shaped supports, for example having a substantially rectangular shape, suitably inclined one relative to one another. Advantageously, the inclination between the two plate-shaped supports can be adjustable, so as to enable an adaptation to different positions required by the specific operational circumstances.

The second portion 610b may be pivotably mounted on the first portion 610a about a rotation axis A extending transversally to the prevailing direction of development D1 of the leg of the patient.

Preferably the first and/or the second portion 610a, 610b have retaining means 611 for keeping the leg and/or the foot in the proper position.

As shown by way of example in FIG. 10, the retaining means 611 can be obtained by suitable bands, which prevent the leg and the foot of the patient to move from the respective first and second portions 610a, 610b of the frame 610.

Preferably the retaining means 611 associated with the first portion 610a are configured to operate with corresponding adjustment means, which enable an axial/longitudinal movement of the retaining means, so as to make it possible to adapt the position of the retaining means to the size of the patient's leg, and in particular to the length of the latter.

For example, the adjustment means may enable for a mutual displacement, along the first portion 610a of the frame 610, of a pair of retaining bands being part of the aforementioned retaining means.

With reference to the frame 610, a main operative plane is defined, which is the plane on which there lie the prevailing direction of development D1 of the leg of the patient and the prevailing direction of development D2 of the patient's foot.

In other words, the main operative plane can be identified as a plane substantially orthogonal to the planar development of the first portion 610a and the planar development of the second portion 610b of the frame 610.

The apparatus 600 comprises a blade 620 (FIGS. 11b, 11c, 11d) mounted on the frame 610 and configured to cut an end of the tibia of the patient.

The blade 620 has, in a projection on the main operative plane, a determined curvature C1. This determined curvature C1 has its concavity facing towards the second portion 610b of the frame 610.

In practice, the curvature C1 of the blade 620 corresponds to the shape that must be given to the terminal portion of the tibia of the patient through the cutting operation performed using the blade 620

The apparatus 600 also comprises a first guide 630 and a second guide 640, associated to the blade 620 to enable the same to operate the desired cut.

The first guide 630 is mounted on said frame 610 and is adapted to impose to the blade 620 a movement according to a first trajectory T1. This first trajectory T1, defined on a plane parallel to said main operative plane, comprises at least one line having a curvature C2 substantially equal to the determined curvature C1, i.e., the curvature presented by the blade 620.

In more detail, the first guide 630 comprises a pair of guide elements 631, 632, each having a respective groove 631a, 632a defining at least said first trajectory T1. In other words, each groove 631a, 632a comprises a portion shaped in a manner substantially identical to the curvature C1 of the blade 620.

Preferably the guide elements 631, 632 are longitudinally movably mounted on the first portion 610a of the frame 610, and the frame 610 includes at least one immobilization means 637 configured for immobilizing the guide elements 631, 632 on the frame 610. The first portion 610a of the frame 610 may for example include two longitudinal elements 638 each configured for supporting a respective guide element.

Preferably each groove 631a, 632a also has additional portions, which extend from one end or from both ends of the portion defining the trajectory T1.

In the preferred embodiment, each groove 631a, 632a has a first substantially straight portion, followed by the portion that defines the first trajectory T1, in turn followed by a further substantially straight portion.

Preferably one of the guide elements or both the guide elements 631, 632 is/are equipped with one or more movable end-of-stroke elements 633, 634, 635, 636. In this way it is possible to precisely adjust the beginning and the end of the first trajectory T1, depending on the specific needs of each intervention.

Advantageously a pair of movable end-of-stroke elements 633, 634; 635, 636 is provided for each guide element 631, 632.

In the preferred embodiment, the guide elements 631, 632 have an elongated shape extending from the first portion 610a of the frame 610.

The second guide 640 is mounted on the frame 610; preferably the second guide 640 can be mounted on the retaining means prearranged at the first portion 610a of the frame 610. The second guide 640 is configured to be disposed above a frontal part of the tibia of the patient when the leg of the patient is supported on the first portion 610a of the frame.

The second guide 640 imposes to the blade 620 a second trajectory T2 on a plane substantially orthogonal to the main operative plane and parallel to the prevailing direction of development of the leg D1 (i.e., in practice, a substantially horizontal plane or parallel to the floor).

The second trajectory T2 is arc-shaped and has a concavity facing towards the second portion 610b of the frame 610, i.e., towards the patient's foot.

Preferably the second guide 640 comprises a guide body 641, for example of a substantially parallelepiped shape, having a slot 642 defining the second trajectory T2.

The blade 620 is adapted to be inserted in the slot 642 to follow the second path T2.

Preferably, the apparatus 600 further comprises a support element 650 to support the blade 620. In particular, the support element 650 may be equipped with a gripping portion, to facilitate the use by the surgeon.

The support element 650 is advantageously engaged with a third guide 660.

The third guide 660 has opposite ends 661, 662, each engaged with a respective guide element 631, 632 and movable along the respective groove 631a, 632a.

The support element 650 is constrained to the third guide 660 and movable along the same.

Preferably, the third guide 660 has an arched shape with concavity facing towards the first portion 610a of the frame 610.

Preferably, the apparatus 600 further comprises a feeler device 670 (FIG. 11) mounted on the frame 610 and movable along the first portion 610a of the frame 610.

The feeler device 670 enables to identify of the area of the top of the tibia, so as to locate the starting point for carrying out the cutting of the tibia using the blade 620.

The feeler device 670 has a substantially arc-shaped shape, extending on a plane substantially orthogonal to the cited main operative plane. Advantageously, the feeler device 670 has a first end constrained to the frame 610 and a second end configured to follow the bony profile of the tibia and identify the highest point thereof (i.e., the point farthest from the first portion 610a of the frame 610). The first end, in particular, is constrained to the first portion 610a of the frame 610. In this way, the feeler device 670 is sufficiently stable and can thus allow identifying in a precise and reliable way the point from where the cut is to start.

Preferably, the apparatus 600 further comprises a distractor device 680 (FIG. 11a) suitable to exert a force of mutual spacing between the foot and the tibia of the patient.

Preferably the distractor device 680 is applied to the talus and is gradually displaced in the direction of the foot, resulting in a gradual and measured distraction of the articulation.

In this way accessibility and visibility of the area where the operation is to be carried out are ensured.

FIG. 26 shows a second embodiment of the surgical apparatus 600 which differs from the first embodiment shown on FIGS. 10 to 11d mainly in that the surgical apparatus 600 is devoid of the guides 630 and 660, in that the guide 640 is directly fixed to the tibia, and in that the guide body 641 further includes a curved guiding surface 643 adjacent the slot 642 and defining at least in part the second trajectory T2. According to said second embodiment, the blade, and more particularly the support element 650, can be freely manipulated by the surgeon.

FIGS. 27 and 28 show a third embodiment of the surgical apparatus 600 which differs from the second embodiment shown on FIG. 26 mainly in that the guide 640 is mounted on the frame 610 and in that the slot 642 is rectilinear. According to said the third embodiment of the surgical apparatus 600, the guide body 641 further includes a support member 644 longitudinally movably mounted on the first portion 610a of the frame 610, and configured for supporting the guide body 641. The support member 644 may for example have an inverted U-shape, and includes two side arms 644a respectively mounted on the first portion 610a of the frame 610, and a central arm 644b connected to the side arms 644a and configured for supporting the guide body 641. Advantageously, the frame 610 includes at least one immobilization element configured for immobilizing the support member 644 on the frame 610.

According to the third embodiment, the guide 640 includes a movable member 645 movably mounted on the central arm 644b of the support member 644 along a first direction extending substantially orthogonally to the prevailing direction of development D1 of the leg of the patient. The guide body 641 is movably mounted on the movable member 645 along a second direction extending substantially parallely to the prevailing direction of development D1 of the leg of the patient.

According to the third embodiment, the guide 640 includes an immobilization element 646 configured for immobilizing the movable member on the support member 644, and an immobilization element 647 configured for immobilizing the guide body 641 on the movable member 645.

Such a configuration of the support member 644, the movable member 645 and the guide body 641 allows the surgeon to adjust easily the position of the guide body 641 relative to the tibia before cutting the latter.

FIG. 29 shows a fourth embodiment of the surgical apparatus 600 which differs from the previous embodiment mainly in that the second portion 610b is articulated relative to the first portion 610a about three non-parallel rotation axes. Such a configuration of the frame 610 allows the surgeon to adjust easily the position of the foot, and notably the flexion, extension, varus and valgus of the foot.

From the operational point of view it should be noted the following.

The patient is made to settle such that his/her leg rests on the first portion 610a of the frame 610 and his/her foot rests on the second portion 610b of the frame 610.

If necessary, the retaining means are adjusted, to ensure stability to the position of the limb.

The distractor device 680 is then operated, so as to improve, as said, accessibility and visibility of the area in which the surgeon will have to operate.

By means of the feeler device 670 the starting point to make the cut is located.

At this point, the blade 620 is used to carry out the cut according to the desired profile.

As shown in FIG. 25, cutting is performed in such a way to give the terminal portion of the tibia an arched shape, so as to preserve the third malleolus. The profile followed in the cutting operation is indicated in the figure by a dashed line. Otherwise, in the case of the same initial situation shown in FIG. 23, the cuts usually applied according to the state of the art are substantially flat (FIG. 24), and therefore imply complete elimination of the third malleolus.

The blade 620 is then inserted in the slot 642 of the guide body 641, in order to enable the second trajectory T2 to be described. This operation can be carried out by displacing the support element 650 along the third guide 660.

The blade is also moved in a way to describe the first trajectory T1. This operation can be carried out by moving jointly the support element 650 and the third guide 660 so that the ends 661, 662 of the latter slide in the grooves 631a, 632a of the guiding elements 631, 632.

In this way it is possible to obtain a cut as the one schematically shown in FIG. 25.

The tibial component 100 can then be applied, in such a way that the expansions 120, 130, 140 get into the inner part of the bony cortex of the tibia.

The intermediate component 300 can be simultaneously engaged with the tibial component 100.

As regards the preparation of the talus, the tool 500 is positioned on the part of the talus facing the tibia.

By means of a suitable tool, in itself known, and by following the front recess 511, the side recesses 512, 513 and the rear recess, it is possible to obtain a shape of the talus that is substantially complementary the talar component 200 which have to be applied.

Depending on the type of component 200 that is to be applied a tool 500 of appropriate shape is used.

In particular, to apply the talar component of FIG. 9 the tool of FIG. 21 will be used, while for applying the talar component of FIG. 20 the tool of FIG. 22 will be used.

In the case in which the tool of FIG. 21 is used, a further small machining may be necessary, aimed at eliminating bony residues that remained at the parts of the active portion 510 which separate the front portion 512a of the first side recess 512 from the rear portion 512b of the same first side recess 512, and the front portion 513a of the second side recess 513 from the rear portion 513b of the same second side recess 513.

The invention achieves important advantages.

First of all, by operating in accordance with a technique based on a frontal approach (rather than a later approach) removal and subsequent reconstruction of bone portions which are not directly affected by the intervention (e.g. fibula) can be avoided.

Furthermore, by means of the type of curved cut herein described and claimed, it is possible to preserve the third malleolus, which would be instead removed by using a traditional flat cut.

A further advantage emerges by observing that the prosthesis according to the invention has perfectly anatomical shape, and therefore allows to completely restoring the articular mobility/functionality after its installation.

The invention claimed is:

1. An ankle prosthesis comprising:
   a tibial component comprising a substantially plate-like main body having a top surface adapted to engage with one end of a tibia, and a bottom surface adapted to engage with other components of said prosthesis, said main body having a substantially quadrilateral profile in a top view, which is delimited by a front side, a rear side and a pair of flanks, said front side being longer than said rear side, said top surface being curved extending from said front side to said rear side, the concavity of said top surface facing towards said bottom surface, wherein said main body has several spikes extending from said top surface without coming into contact with any one of said sides or flanks of said main body, the several spikes being configured to engage with the inner part of the bony cortex of the tibia, and
   a talar component comprising a talar main body with a talar top surface and a talar bottom surface, wherein the talar bottom surface is of quadrilateral shape and is delimited by a talar front side, a talar rear side, and a first talar flank and a second talar flank, wherein the talar main body further includes several talar spikes configured to directly engage with a patient's talus and extending from said talar bottom surface, wherein said talar top surface is curved extending from said talar front side to said talar rear side, the concavity of said talar top surface facing towards said talar bottom surface.

2. The ankle prosthesis according to claim 1, wherein the front side, the flanks and the rear side of the main body are substantially curvilinear.

3. The ankle prosthesis according to claim 1, further comprising an intermediate component configured to enable mutual cooperation and movement between the tibial component and the talar component.

4. The ankle prosthesis according to claim 3, wherein a top surface of the intermediate component is shaped substantially complementary to the bottom surface of the main body of the tibial component, and the talar top surface of the talar main body of the talar component is shaped substantially complementary to a bottom surface of the intermediate component.

5. The ankle prosthesis according to claim 1, wherein the bottom surface of the main body of the tibial component has a development similar to that of the top surface of the main body of the tibial component.

6. The ankle prosthesis according to claim 1, wherein the first talar flank has a curvature larger than a curvature of the second talar flank.

7. The ankle prosthesis according to claim 1, wherein the talar front side is longer than the talar rear side.

8. The ankle prosthesis according to claim 1, wherein the tibial component and the talar component are implantable using a frontal approach.

9. An ankle prosthesis comprising:
   a tibial component comprising a substantially plate-like main body having a top surface adapted to engage with one end of a tibia, and a bottom surface adapted to engage with other components of said prosthesis, said main body having a substantially quadrilateral profile in a top view, which is delimited by a front side, a rear side and a pair of flanks, said front side being longer than said rear side, said top surface being curved extending from said front side to said rear side, the concavity of said top surface facing towards said bottom surface, said bottom surface being curved extending from said front side to said rear side, the concavity of said bottom surface facing towards said bottom surface, wherein said main body has several spikes extending from said top surface without coming into contact with any one of said sides or flanks of said main body, the several spikes being configured to engage with the inner part of the bony cortex of the tibia, and
   a talar component comprising a talar main body with a talar top surface and a talar bottom surface, wherein the talar bottom surface is of quadrilateral shape and is delimited by a talar front side, a talar rear side, and a first talar flank and a second talar flank, wherein the talar main body further includes several talar spikes configured to directly engage with a patient's talus and extending from said talar bottom surface, wherein said talar top surface is curved extending from said talar front side to said talar rear side, the concavity of said talar top surface facing towards said talar bottom surface,
   wherein the tibial component and the talar component are implantable in a frontal approach.

10. The ankle prosthesis of claim 9, wherein the talar main body includes several sequences of talar spikes configured to directly engage with a patient's talus and extending from said talar bottom surface.

11. The ankle prosthesis of claim 9, wherein the talar main body includes:
   a front sequence of talar spikes configured to directly engage with a patient's talus and extending from said talar bottom surface, the talar spikes of the front sequence being substantially aligned; and
   a rear sequence of talar spikes configured to directly engage with a patient's talus and extending from said talar bottom surface, the talar spikes of the rear sequence being substantially aligned.

* * * * *